United States Patent [19]

Hanson

[11] Patent Number: 4,526,448
[45] Date of Patent: Jul. 2, 1985

[54] VISITOR SPECTACLES

[75] Inventor: George N. Hanson, New York, N.Y.

[73] Assignee: Eastern Safety Equipment Co., Inc., Long Island City, N.Y.

[21] Appl. No.: 416,193

[22] Filed: Sep. 9, 1982

[51] Int. Cl.³ ............................ G02C 5/22; G02C 5/14
[52] U.S. Cl. ..................................... 351/153; 351/121
[58] Field of Search .................. 351/153, 121; 16/228

[56] References Cited

U.S. PATENT DOCUMENTS 2,166,110  7/1939  Baldanza ..................... 351/111 UX
2,382,962  8/1945  Courtney ............................ 2/448 X

FOREIGN PATENT DOCUMENTS 914793  10/1946  France ................................ 351/153

*Primary Examiner*—Rodney B. Bovernick
*Attorney, Agent, or Firm*—Paul J. Sutton

[57] ABSTRACT

The present invention provides an improved assembly for rotatably connecting temple members of protective visitor spectacles to a lens body. First and second means for rotatably connecting each temple member to the lens body of the rotation between open and closed positions are provided. The first means connects the top portion of the side rim of the lens body with the upper portion of the first edge of a wrap-around side-shield of the temple member via a pair of flanges provided with a pin and hole. The second means connects the bottom portion of the side rim of the lens body with the lower portion of the front edge of the side shield. The second means includes an upwardly projecting hook member connected to the side rim of the lens body engaging a recess found along the bottom edge of the side shield. The hook member rotates in the recess and exerts an upward pressure against the temple member keeping the temple member engaged at the first connecting means.

7 Claims, 7 Drawing Figures

VISITOR SPECTACLES

The present invention relates generally to protective spectacles given to a visitor of an industrial site of any kind, including shops where machining, welding, or similar activity is taking place. In particular, the invention relates to an improved assembly for protective spectacles for visitors.

Before a visitor to a plant goes into the plant work area, he is given a pair of inexpensive safety spectacles to wear during the visit to help insure that injurious particles are intercepted before they reach the eyes. These type of safety spectacles are a lightweight, comfortable type that are intended for brief viewing use and are not intended to withstand heavy use nor are these type of spectacles intended for close-up viewing. It also generally includes wrap-around side shields. These spectacles are made usually of a clear plastic such as polypropaline or polycarbonate. Because most often the spectacles are not used more than once or twice, cost of manufacture is an important consideration in their design. Safety, however, cannot be sacrificed for cost.

One method of keeping down the cost of the mass production of these spectacles is to keep the molding process to as few elements as possible. One type of visitor spectacles comprises a lens body including the two clear lenses and two temple members rotatably joined to the lens body by top and bottom rotatable hinges of identical snap-in or "self-reinforcing" design. This type of hinge, developed by the Norton Company, has one flange extending from the top hinge of the temple member provided with an upwardly extending pin mating with a hole in the flange extending from the top edge of the lens body. At the bottom, a flange extending from the bottom of the protective wrap-around side-shield is attached to the temple member and is provided with a downwardly extending pin mating with a hole formed in another flange extending from the bottom side of the lens body. The spectacles are flexible and the two pins snap into the holes. Thus, this solution has two pin hinges providing horizontal rotation and opposing vertical pressures. A problem with this solution, however, is that the lens body cannot be cast in a single mold, but the flanges with the pin holes must be set on in a second operation, a cost-adding procedure. Also, the inwardly extending bottom hinge makes wearing the visitor spectacles difficult when the visitor places them over prescription eyeglasses.

Another attempt to reduce the cost of hinging the temple member is one marketed by Eastern Safety Equipment Co., Inc. This method of hinging the temple members concentrates the hinging task at the top portion of the lens body and also the temple member. Here a double hinge extends transversely from the lens body with opposing holes. The temple member is provided with a flange with a double opposed pin that is slid between the two lens body flanges and, by pressuring the biasable body flanges the temple member flange pin is snapped into the holes of the flange of the lens body. The flanges then come together holding the temple member and the lens body. In this design the temple member is held by upward and downward pressures at the top portion of the lens body only. The downwardly extending side shield is not attached at the bottom of the shield to the lens body. Although this method is functional, it has two disadvantages. One is that the lens body cannot be cast in one mold because of the double flange construction. Another disadvantage is that the bottom portion is not quite as strongly mounted as it might be. Also a certain levering action can occur at the double flanged top portion when the bottom portion of the temple member at times is pulled away from the lens body. The present invention contemplates the elimination of most of all of these limitations and disadvantages of conventional solutions to recognized needs of the art by providing a novel hinge assembly for rotatably attaching the temple member to the lens body.

Accordingly, it is an object of my invention to provide a relatively inexpensive hinge assembly for rotatably attaching a temple member to a lens body of a visitor spectacles assembly.

Another object of the present invention is to provide a novel means for connecting both the upper and lower portions of a side shielding wall of a temple member so that both the lens body and the temple members can be molded in each one's single mold, thus reducing assembly cost.

Yet another object of this invention is to provide a novel means for rotatably connecting and mounting a temple member to a lens body at the lower portion of the side shield wall.

Yet another object of my invention is to provide a method of rotatably connecting a temple member to a lens body by means of a conventional flanged pin and hole assembly at the upper portion of the assembly and a recessed catch means in both the lens body and the temple member at the lower portion of the assembly.

Another object of my invention is to provide a standard pin and hole flange rotatably connected at the upper portion of a lens body and temple member a rotatable bottom connection between the lens body and the temple member that allows the lens body and each temple member to be molded in one cylindrical mold and then snap-on assembled.

Another object of my invention is to reduce the cost of manufacture of visitor spectacles by providing a novel means for rotatably connecting both the top and bottom portions of the lens body to the side shield wall of a temple member so that the lens body may be cast in a single cylindrical mold.

Yet another object of my invention is to provide a flexible lens body that receives a temple member by snap-on assembly technique and that requires only a single mold for the lens body and one for the temple member so that manufacturing costs are significantly reduced.

The present invention fulfills the above objects and overcomes limitations and disadvantages of prior art solutions to problems by providing first and second means for rotatably connecting each temple member to the lens body for rotation between an open position and a closed position. The first means is for rotatably connecting the top portion of the side rim of the lens body with the upper portion of the front edge of a wrap-around shield, or wall, of the temple member. The first means also exerts a downward pressure on the lens body on the temple member and exerts an upward pressure from the temple member on the lens body. The first means includes a pair of flanges with a pin and mating hole.

The second means is for rotatably connecting the bottom portion of the side rim of the lens body with the lower portion of the front edge of the protective wall. The second means includes a hook means connected to the bottom portion of the side rim of the lens body. The wall of the temple member has a bottom edge intersecting the side edge, the wall forming a first recess at the bottom edge. The first recess has a downwardly facing opening and an inner surface. The hook means is for engaging the first recess in rotatable connection and for exerting an upward pressure against the inner surface of the first recess equal to the downward pressure exerted by the first means for rotatable connection.

This invention will be more clearly understood from the following description of specific embodiments of the invention, together with the accompanying drawings, wherein similar reference characters elements throughout the several views, and in which.

With references now to a detailed description of the drawings, the following description occasionally will for the convenience of the reader refer to certain elements of the assembly as being located vertically or horizontally or upper and lower with the idea being that the wearer of the spectacles is generally wearing the spectacles in a substantially upright position; this terminology therefore does not imply that the spectacles are not tilted at other angles during use and that the terms are for purposes of exposition only.

Figure 7:
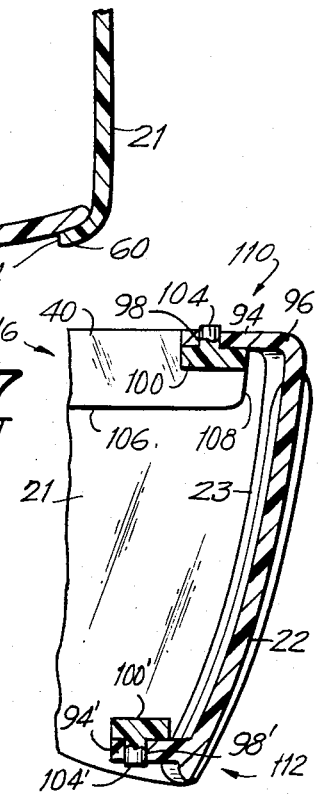
FIG. 7 is a front sectional view of the upper and lower connections of the prior art.

A brief discussion of the prior art as illustrated in FIG. 7 is contained at the end of the detailed discussion.

Figure 1:
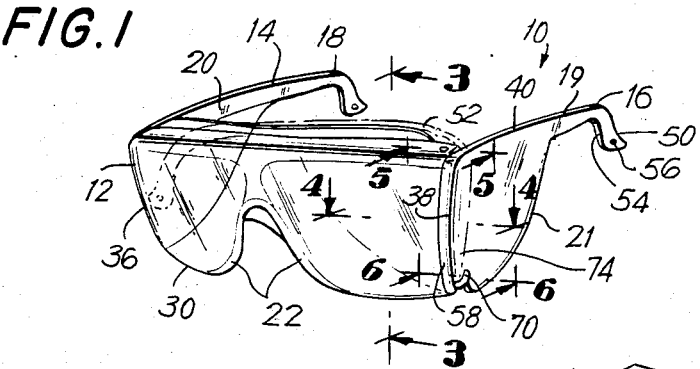
FIG. 1 is a perspective view of the visitor spectacles assembly showing one temple member attached to the lens body.
Figure 3:
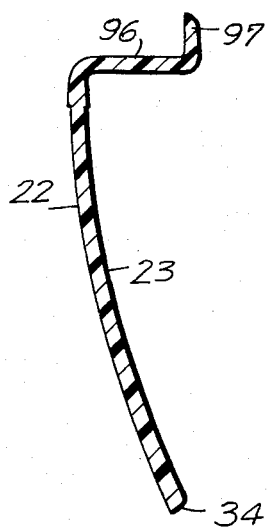
FIG. 3 is a side sectional view of the lens body taken at line 3—3 in FIG. 1.
Figure 4:
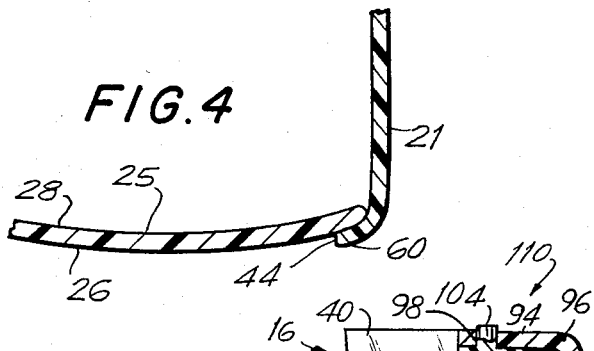
FIG. 4 is a sectional view of the lens body and the shield wall of the temple member taken at line 4—4 of FIG. 1.
Figure 5:
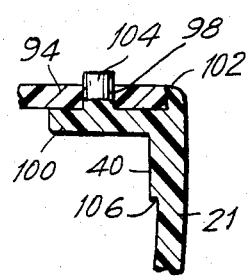
FIG. 5 is a front sectional view of the top rotatable connection taken at line 5—5 in FIG. 1.
Figure 6:
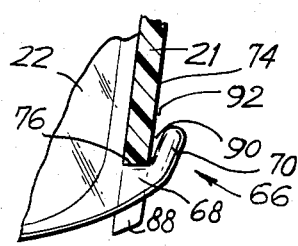
FIG. 6 is a front sectional view of the lower rotatable connection taken at line 6—6 in FIG. 5.

FIG. 1 illustrates in a partially perspective view, protective, or safety, visitor spectacles assembly 10 comprising a lens body 12 and a pair of temple members 14 and 16. Each of these temple members, 14 and 16, includes an elongated bar 18,19 and a bottom wrap-around side-shield, or bottom wall, 20, 21 respectively. For purposes of exposition, most of the discussion herein will be directed to temple member 14 in order to avoid redundancy; it is intended that all descriptions of temple member 14 will apply likewise to temple member 16. Lens body 12 and temple members 14 and 16 are each preferably made of a resilient, impact resistant material such as polypropylene or polycarbonate. These plastic materials are also clear, as lens body 12 includes a pair of lenses, lens 22 and lens 24, which are connected to temple members 14 and 16 respectively in a manner to be described. Lenses 22 and 24 are double convex in order to allow the visitor a non-distorted view, even when wearing prescription glasses. This double convexity is illustrated in vertical convexity 23 as shown in FIG. 3 and horizontal convexity 25 as shown in FIG. 4. Lenses 22 and 24 each have front surface 26 and and opposite rear surface 28, the front surface being on the side opposite the user and the rear surface on the side of the user. Lens body 12 has a rim 30 that extends around the periphery of the lens body and includes intersecting top rim 32, bottom rim 34, and side rims 36 and 38. Temple member 14 includes an elongated temple bar 40 that extends laterally from top portion 42 of side rim 36 of lens 24. Bottom portion 43 of side rim 36 is substantially opposite top portion 42. Wrap-around side shield, or bottom wall, 21 is connected to the underside of temple bar 19. Wall 21 which has the purpose of protecting the eyes of the user from the side, includes a front side edge 44 having an upper portion 46 and an opposed lower portion 48, that are substantially in alignment with top and bottom portions 42 and 43 of side rim 38. Temple members 14 and 16 are each rotatable between an open position 50 wherein the bar 19 is substantially transverse to lens body 12 in position to be worn by user, as illustrated in phantom lines in FIG. 1; and a closed position 52 wherein bar 19 is substantially lateral to lens body 12, as shown in solid lines in FIG. 1. Temple bar 19 includes a downwardly curved rearwardly positioned portion 54 which is configured to pass over and downwardly behind the ear of the user. Hole 56 is optionally formed across curved portion 54 of bar 19 to hold a cord (not shown) for supporting the spectacles assembly. In the open position, front edge 44 of wall 21 of temple member 16 is in juxtaposition with side rim 38 of lens body 12. As will be discussed below, a vertical lip 60 extends forwardly around front surface 26 of lens body 12 in the open position; front edge 44 is the edge of lip 60. In the closed position front edge 44 is seperated from side rim 38 by space 58. Wall 21 includes a vertical overlapping lip 60, seen in FIG. 4, that extends from wall 21 a short distance around front surface 26 of lens 24 when the temple member is in the open position. Front edge 44 of wall 21 is disposed at the edge of lip 60 in the preferred embodiment.

Temple member 16, and as stated above, temple member 14 as well, is rotatably connected to lens body 12 by an upper, or first means 62 and a lower, or second lower means 64; the upper and lower means rotate the temple members between the open and closed positions 50 and 52. The upper means 62 is for rotatably connecting top portion 42 of side rim 38 of lens body 12 with upper portion 46 of front edge 44 of wall 21. First means 62 is also for exerting a downward pressure from lens body 12 on temple member 16. Second means 64 is for rotatably connecting bottom portion 43 of side rim 38 of lens body 12 with lower portion 48 of front edge 44 of wall 21; the second means is also for exerting an upward pressure from lens body 12 on temple member 16 equal to the downward pressure exerted as mentioned. Second means 64 includes a hook 66 connected to bottom portion 43 of side rim 38. Hook 66 includes arm 68 extending laterally from bottom portion 43 of side rim 38 and an upwardly extending first finger 70 connected to the end of arm 68. Wall 21 has an inner surface 72 on the user, or open side of the wall and an opposed outer surface 74.

Figure 2:
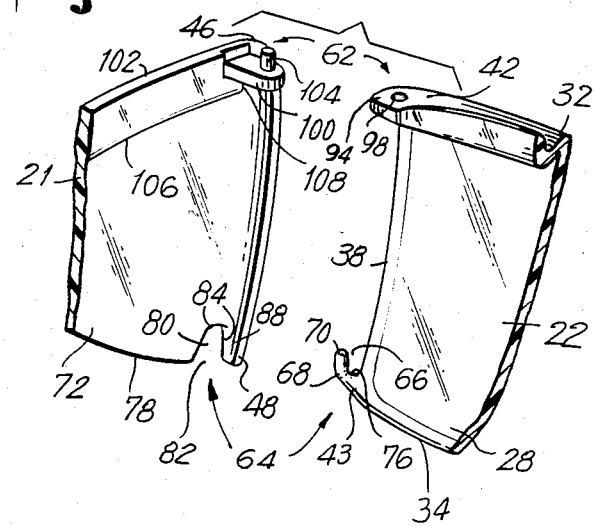
FIG. 2 is a partial exploded perspective view of the upper and lower rotatable connecting means showing the details of the upper and lower means for rotatably connecting the lens body with the temple member.

Wall 21 includes lower edge 78, which extends rearwardly from lower portion 48 of intersecting front edge 44 at upward incline to the lower side of bar 19. Recess 80 is formed in lower edge 78 of wall 21 having a downwardly facing opening 82. Hook 66 engages recess 80 in rotatable connection. Also, hook 66 exerts an upward pressure against inner recess surface 84 of recess 80, which is approximately opposite recess opening 82, equal to the downward pressure exerted by upper rotatable means, 62 which will be discussed below. Specifically, first finger 70 is disposed in proximity to outer surface 74 of wall 21 and arm 68 is in contact with inner recess surface 84. Inner surface 84 is shown in FIG. 2 as having wedged sides and a flat upper surface portion, but this configuration may vary without affecting the spirit of the invention.

Recess 80 is further defined by a downwardly extending finger 88 that is disposed between front edge 44 of lower portion 48 of wall 21 and inner recess surface 84. Second finger 88 engages a second recess 90 defined by side rim 38, arm 68, and first finger 70 having upwardly facing opening 92. Second finger 88 extends downwardly from first recess 80 on the front surface of 26 side of lens body 22 so that inner surface 84 of first recess 80 is in contact with arm 68 and a downward pressure is exerted on lens body 12 from temple member 16. Likewise, an upper force is exerted on temple member 16 from lens body 12.

First, or upper means 62 for rotatably connecting temple member 16 to lens body 12 includes a first flange 94 connected to top rim 32 of lens body 12. Lens body 12 is preferably provided with horizontal anti-glare brow guard, horizontal shelf element 96, including a vertical brow band 97. Shelf element 96 extends horizontally inwardly from rear surface 28 of top rim 32, with shelf element 96. A vertical hole 98 is formed in first flange 94. A second flange 100 is connected to upper edge 102 of temple member 16 adjacent to front edge 44 and includes an upwardly extending pin 104 in alignment within hole 98. Second flange 100 is disposed inwardly transverse to temple member 16. Also, second flange 100 is approximately transverse to first flange 94 in the open position of assembly 10 and substantially opposed to first flange 94 in the closed position. First and second flanges 94 and 100 are in bearing contact as will be explained.

During assembly of the spectacles, the lower, or second connecting means 64 are first mounted by sliding first and second fingers 70 and 88 over first and second recesses 80 and 90 so that arm 68 of second recess 90 bearingly engages inner recess surface 84 of first recess 80. Then the top of pin 104 of second flange 100 is slid to bearingly engage the bottom of first flange 94. Temple member 16 is pressured against arm 68 of lens body 12 during assembly while first flange 94 is pressured upwards into a biased position. Pin 104 is slid into hole 98, at which time the upper first flange 94 snaps back into unbiased position so that temple member 16 is pressure gripped by lens body 12 by an upward pressure at arm 68 at second recess 90 and an equal downward pressure from first flange 94 at second flange 100. It can also be stated that temple member 16 is kept positioned adjacent to side rim 38 of lens body 12 by equally outwardly exerted upward and downward pressures at first flange 94 from second flange 100 and arm 68 from inner recess surface 84 of temple member 16. These opposing pressures are initially created by the trapping of the pin 104 of temple member 16 and biasedly pressuring the temple member 16 between the first and second rotatable means 62 and 64. Temple member 16 is also thus rotatable about pin 104 and at lower rotatable means 64 between the open and closed positions.

In the closed position 52, upwardly projecting first finger 70 is in contact with or proximate to outer surface 74 of shield wall 21. In the open position, first finger 70 is in bearing contact with outer surface 74 so that temple member 16 is aided in being prevented from being rotated past the open position. Also, downwardly projecting second finger 88 is in bearing contact with front surface 26 of lens body 12 when temple member 16 is in open position 62, thus aiding in preventing the temple member from being rotated past the open position. In addition, upper position 46 of front edge 44 of lip 60 is likewise in bearing contact with front surface 26 when temple member is in the open position. Temple bar 18 preferably extends along the top of temple member 16 forming a slight horizontal ledge 106 with wall 21 and a vertical ledge 108 proximate to first flange 70, so that when the temple member is rotated past the open position, vertical ledge meets side rim 38 of lens body 12 and prevents further rotation.

An illustration of the top and bottom connecting means is shown in FIG. 7. The top portion is shown with the same identifying numerals as used in the discussion of first connecting means 50 of the present invention; the bottom portion, because it is an effect a reverse construction of the top portion, is shown with the identifying numerals of comparative elements in prime numerals. Specifically, a first flange 94 with hole 98 of lens body 22 is rotatably connected to a second flange 100 of temple member 16 with an upwardly extending pin 104 positioned in hole 98 at the upper area 110 of the prior art assembly connection. In the lower area 112, a first flange 94' with a hole 98' of lens body 22 is rotatably connected to a second flange 100' of temple member 16 with a downwardly extending pin 104' positioned in hole 98'. The improved connection of the present invention is readily observed with the connection at lower area 112 being replaced by the novel and simple rotatable connector of the present invention.

The above discussion, as before noted, is centered on temple member 16, for purposes of exposition but all the elements discussed relating to member 16 apply likewise to the outer temple member 14.

The embodiment of the invention particularly disclosed and described above is presented merely as an example of the invention. Other embodiments, forms, and modifications of the invention coming within the proper scope and spirit of the appended claims will, of course, readily suggest themselves to those skilled in the art.

What is claimed is:

1. An improved assembly for protective spectacles of the type comprising a lens body made of a resilient material and a pair of temple members rotatably connected to the lens body, the lens body including a pair of lenses having front and rear surfaces, each lens having a side rim with top and bottom portions, each temple member including a protective side wall having a front edge with an upper portion and a lower portion and an enlarged horizontal bar extending inwardly from said side wall, said temple member being rotatable between an open position wherein the temple member is substantially transverse to the lens body and a closed position wherein the temple member is substantially lateral to the lens body, a side edge of said temple member being in juxtaposition with the side rim of said lens body in the open position and spaced from the side rim of the lens body in the closed position, the improved assembly, in combination, comprising:

first and second means for rotatably connecting each said temple member to said lens body for rotation between said open and closed positions,
said first means including a pin and hole connection for rotatably connecting said top portion of said side rim of said lens body with said upper portion of said front edge of said side wall of said temple member, said first means exerting a downward pressure from said lens body on said temple member, and said temple member exerting an upward pressure on said lens body, said second means rotatably connecting said bottom portion of said side rim of said lens body with said lower portion of said front edge of said wall, said second means including hook means having a rounded pivoting surface connected to said bottom portion of said side rim, said wall having a bottom edge intersecting said side edge, said wall forming a first rounded recess rotatably conforming to said rounded surface of said hook means, and disposed at said bottom edge, said first recess having a downwardly facing opening and an inner surface, said hook means being for engaging said first recess in rotatable connection and for exerting an upward pressure against said inner surface of said first recess substantially equal to the downward pressure exerted by said first means.

2. An upward assembly for protective spectacles according to claim 1, wherein said hook means includes an arm extending laterally from said bottom portion of said side rim and an upwardly extending first finger connected to the end of said arm, said wall having an outer surface, said finger being disposed in proximity to said outer surface and said arm being in bearing contact with said inner surface of said recess, whereby said temple member is rotatable between the open and closed positions and the arm exerts an upward pressure on the temple member substantially equal to the downward pressure exerted by the first means for rotatably connecting.

3. An improved assembly for protective spectacles according to claim 2, wherein said arm, said first finger, and said side rim define a second recess having an upwardly facing opening, and said first recess is further defined by a downwardly extending second finger disposed between said front edge of said lower portion of said wall and said inner surface, said second finger engaging said second recess in rotatable connection, wherein said second finger extends downwardly from said first recess in proximity to said front surface of said lens body and said inner surface of said first recess is in bearing contact with said arm, whereby said inner surface exerts a downward pressure on the arm and the lens body equal to the upward pressure exerted by the first means for rotatably connecting.

4. An improved assembly for protective spectacles according to claim 3, wherein said first means for rotatably connecting includes, said lens body having a substantially horizontal top rim intersecting said side rim a first flange adjacent to said side rim connected to said top rim extending horizontally inwards from said rear surface, said first flange forming a vertically disposed hole, and said temple member having a substantially horizontal upper edge intersecting said first edge, and a second flange connected to said upper edge adjacent to said front edge of said wall, said second flange extending approximately transversely to said temple member and substantially opposed to said first flange in said closed position, said second flange including an upwardly extending pin positioned in said hole of said first flange said first and second flanges being in bearing contact, wherein said first flange exerts a downward pressure on said second flange and on said temple member and said second flange exerts an upward pressure on said first flange and on said lens body.

5. An improved assembly for protective spectacles according to claim 4, wherein said top rim of said lens body is provided with a shelf member extending transversely inwardly from said rear surface, said first flange being unitary with said shelf member.

6. An improved assembly for protective spectacles according to claim 5, wherein said wall includes an outer surface, wherein in said open position said first finger is in bearing contact with said outer surface and said second finger is in bearing contact with said front surface of said lens body, whereby said temple member is further prevented from being rotated beyond said open position.

7. An improved assembly for protective spectacles according to claim 6, wherein a projecting vertical lip extends transversely from said wall, said front edge extending along said lip, and said second finger extending downwards from said lip.

* * * * *